United States Patent [19]

Adelstein et al.

[11] Patent Number: 4,772,619

[45] Date of Patent: Sep. 20, 1988

[54] [(1H-BENZIMIDAZOL-2-YLSULFINYL)METHYL]-2-PYRIDINAMINES

[75] Inventors: Gilbert W. Adelstein, Evanston; Alan E. Moormann, Skokie; Stella S. T. Yu, Morton Grove, all of Ill.

[73] Assignee: G. D. Searle & Co., Chicago, Ill.

[21] Appl. No.: 887,780

[22] Filed: Jul. 17, 1986

[51] Int. Cl.$^4$ .................. A61K 31/415; C07D 401/12
[52] U.S. Cl. ..................................... 514/338; 546/271
[58] Field of Search .......................... 514/338; 546/271

[56] References Cited

U.S. PATENT DOCUMENTS

| | | |
|---|---|---|
| 4,045,563 | 8/1977 | Berntsson et al. ............ 546/271 |
| 4,045,564 | 8/1977 | Berntsson et al. ............ 546/271 |
| 4,182,766 | 1/1980 | Krassó et al. ............... 546/271 |
| 4,248,880 | 2/1981 | Krassó et al. ............... 546/271 |
| 4,255,431 | 3/1981 | Junggren et al. ............ 546/271 |
| 4,327,102 | 4/1982 | Crossley ..................... 546/271 |
| 4,337,257 | 6/1982 | Junggren et al. ............ 546/271 |
| 4,359,465 | 11/1982 | Ruwart ..................... 546/271 |
| 4,394,509 | 7/1983 | Crossley ..................... 546/271 |
| 4,472,409 | 9/1984 | Senn-Bilfinger .............. 546/271 |
| 4,575,554 | 3/1986 | Sih .......................... 546/271 |

FOREIGN PATENT DOCUMENTS

| | | |
|---|---|---|
| 903128 | 12/1985 | Belgium . |
| 127763 | 12/1984 | European Pat. Off. . |
| 130729 | 1/1985 | European Pat. Off. . |
| 167943 | 1/1986 | European Pat. Off. ............ 546/271 |
| 3415971 | 8/1984 | Fed. Rep. of Germany . |
| 416649 | 1/1981 | Sweden . |
| 2134523 | 8/1984 | United Kingdom . |
| 2137616 | 8/1984 | United Kingdom . |
| 2161160 | 1/1986 | United Kingdom ............... 546/271 |

OTHER PUBLICATIONS

J. G. Spenney, "Biochemical Mechanisms of Acid Secretion by Gastric Parietal Cells," *J. Clin. Gastro.*, 5 (Suppl. 1), 7-15, (1983).

A. Brandstrom et al., "Structure Activity Relationships of Substituted Benzimidazoles," *Scand. J. Gastroenterol.*, 20 (Suppl. 108), 15-22 (1985).

B. Beilenson and F. M. Hamer, "Thiazenocyanines, Part I. Carbocyanins Containing the 2:4-Benzthiazine Nucleus," *J. Chem. Soc.*, 98-102 (1942).

J. Chandra Rajan and L. Klein, "Determination of Inorganic Phosphorus in the Presence of Organic Phosphorus.," *Anal. Biochem.*, 72, 407-412 (1976).

*Primary Examiner*—Jane T. Fan
*Attorney, Agent, or Firm*—Mary Jo Kanady; Paul D. Matukaitis

[57] ABSTRACT

This invention relates to [(1H-benzimidazol-2-ylsulfinyl)methyl]-2-pyridinamines that are useful in the treatment and prevention of ulcers.

6 Claims, No Drawings

[(1H-BENZIMIDAZOL-2-YLSULFINYL)METHYL]-2-PYRIDINAMINES

BACKGROUND OF THE INVENTION (a) Field of the Invention

This invention relates to compounds that are useful in the treatment and prevention of ulcers. More particularly, this invention relates to [(1H-benzimidazol-2-ylsulfinyl)methyl)-2-pyridinamines that inhibit gastric acid secretion and which are, therefore, useful in the treatment of peptic ulcers. The compounds of this invention directly inhibit acid secretion by parietal cells of the stomach through inhibition of (H+ +K+)-ATPase. For review, see, e.g., J. G. Spenney, "Biochemical Mechanisms of Acid Secretion by Gastric Parietal Cells," *J. Clin. Gastro.*, 5 (Suppl. 1), 7–15 (1983). In addition, some of the compounds of this invention also exert cytoprotective activity. For review of cytoprotection, see, e.g., U.S. Pat. No. 4,359,465.

(b) Prior Art

Heterocyclylalkylsulfinylbenzimidazoles have been disclosed as gastric acid secretion inhibitors. See U.S. Pat. Nos. 4,472,409, 4,394,509, 4,337,257, 4,327,102, 4,255,431, 4,045,564, and 4,045,563; British Pat. No. 2,134,523; German Offenlegungeschrift No. 3,415,971 and Swedish Pat. No. 416649. Some heterocyclylalkylsulfinylbenzimidazoles have also been disclosed as cytoprotective agents. See U.S. Pat. No. 4,359,465. The following structure is illustrative of compounds disclosed in these patents:

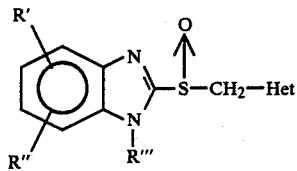

wherein R' and R" represent hydrogen, alkyl, halogen, trifluoromethyl, cyano, carboxy, hydroxy, acyl, and the like; R'" represents hydrogen, alkyl, acyl, alkoxysulfonyl, and the like; and Het represents heterocyclic groups containing at least one endocyclic (ring) nitrogen. No compound disclosed in these patents includes an exocyclic amino function attached to the Het group, a feature characteristic of the compounds of the present invention. Moreover, where the Het function is 2-pyridyl, antisecretory effects are reportedly absent when the pyridine ring is substituted at the 6-position with groups other than the amino groups of this invention. See A. Brandstrom, P. Lindberg, and U. Junggren, "Structure activity relationships of substituted benzimidazoles," *Scand. J. Gastroenterol.*, 20 (suppl. 108), 15–22 (1985).

Heterocyclylalkylsulfinylnaphth[2,3-d]imidazoles have also been disclosed as gastric acid secretion inhibitors. See U.S. Pat. Nos. 4,248,880 and 4,182,766. The compounds disclosed in these patents are related to those illustrated the above structure, except for having a substituted naphth[2,3-d]imidazole group instead of the benzimidazole group. Similarly, other heterocyclylalkylsulfinylbenzimidazoles having a ring fused to the benzimidazole group have been disclosed as gastric acid secretion inhibitors and cytoprotective agents. See European Patent Application Nos. 130,729 and 127,763. Because of the additional ring fusions of these compounds, as well as for the same reasons stated in the preceeding paragraph, the compounds of the present invention are structurally distinguished from prior art compounds cited.

Benzylsulfinylbenzimidazoles have also been disclosed as antiulcer agents. Belgian Pat. No. 903,128. No compounds disclosed in the Belgian patent contain a pyridine ring, a feature characteristic of the compounds of this invention.

The invention relates to compounds of Formula I:

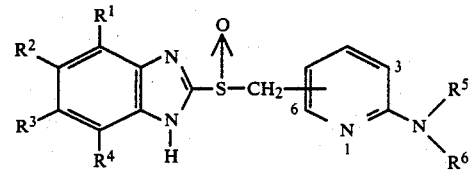

or the pharmaceutically acceptable acid addition salts thereof; or the pharmaceutically acceptable base addition salts thereof;

wherein $R^1$, $R^2$, $R^3$, and $R^4$ are independently:
(a) hydrogen;
(b) $C_1$–$C_6$ alkyl;
(c) $C_1$–$C_6$ alkoxy;
(d) $C_2$–$C_6$ hydroxyalkyl;
(e) $C_1$–$C_4$ fluorinated alkyl; or
(f) halogen; and wherein $R^5$ and $R^6$ are independently:
(a) hydrogen; or
(b) $C_1$–$C_6$ alkyl.

Although the structure shown for Formula I indicates one tautomeric form, it is understood that this representation is for convenience only and that the scope of this invention includes as equivalents all tautomeric forms of the compounds of this invention.

The term "$C_1$–$C_6$ alkyl" refers to straight or branched chain alkyl groups having from 1 to 6 carbon atoms, also referred to as lower alkyl. Examples of $C_1$–$C_6$ alkyl are methyl, ethyl, propyl, butyl, pentyl, hexyl, and the isomeric forms thereof.

The term "$C_1$–$C_6$ alkoxy" refers to straight or branched chain alkoxy groups having from 1 to 6 carbon atoms. Examples of $C_1$–$C_6$ alkoxy are methoxy, ethoxy, propoxy, butoxy, pentoxy, hexoxy, and the isomeric forms thereof.

The term "$C_2$–$C_6$ hydroxyalkyl" refers to straight or branched chain hydroxyalkyl groups having from 2 to 6 carbon atoms. Examples of $C_2$–$C_6$ hydroxyalkyl are 2-hydroxyethyl, 3-hydroxypropyl, 4-hydroxybutyl, 5-hydroxypentyl, 6-hydroxyhexyl, and the isomeric forms thereof.

The term "$C_1$–$C_4$ fluorinated alkyl" refers to straight or branched chain alkyl groups in which one or more hydrogen atoms are replaced with fluorine atoms. Examples of $C_1$–$C_4$ fluorinated alkyl are fluoromethyl, difluoromethyl, trifluoromethyl, 1- or 2-fluoroethyl, 1,1-difluoroethyl, 2,2,2-trifluoroethyl, perfluoroethyl; other similarly monofluorinated, polyfluorinated, and perfluorinated ethyl, propyl, and butyl groups; and the isomeric forms thereof.

Examples of halogen are fluorine, chloride, bromine, and iodine.

The term "pharmaceutically acceptable acid addition salt" refers to a salt prepared by contacting a compound of Formula I with an acid whose anion is generally considered suitable for human consumption. Examples of pharmacologically acceptable acid addition salts include the hydrochloride, hydrobromide, hydroiodide, sulfate, phosphate, acetate, propionate, lactate, maleate, malate, succinate, and tartrate salts.

The term "pharmaceutically acceptable base addition salt" refers to a salt prepared by contacting a compound of Formula I with a base whose cation is generally considered suitable for human consumption. Examples of pharmacologically acceptable base addition salts include lithium, sodium, potassium, magnesium, calcium, titanium, ammonium, alkylammonium, dialkylammomium, trialkylammonium, tetraalkylammonium, and guanidinium salts.

The compounds of this invention may be prepared by the methods illustrated in the following Schemes. Unless otherwise specified, the various substituents are defined as for Formula I, above. Scheme A illustrates the preparation of thio intermediates of Formula IV and of the sulfoxide compounds of this invention, Formula I.

SCHEME A

Thio intermediates of Formula IV may be prepared by at least two routes, each of which involves reaction of a

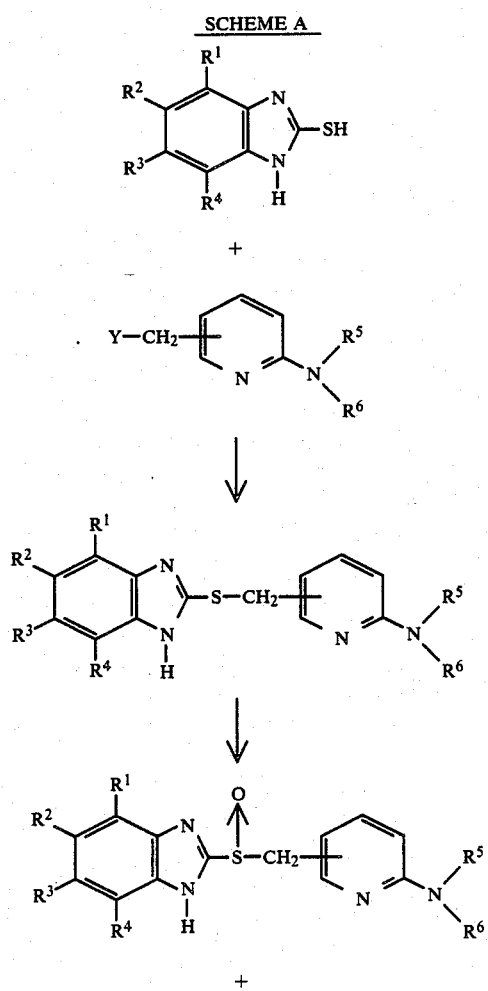

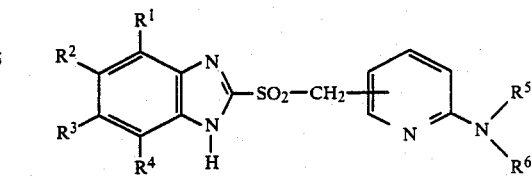

2-mercaptobenzimidazole of Formula II with a compound of Formula III. In the preferred route, the 2-mercaptobenzimidazole of Formula II reacts with a halomethyl-2-pyridinamine (Formula III in which Y is a halogen, preferably chlorine or bromine) in a suitable organic solvent at room temperature. Suitable organic solvents for the reaction are organic liquids in which reactants may be dissolved or suspended but which are otherwise chemically inert. Examples of suitable organic solvents include N,N-dialkylformamide; lower alkanols, such as methanol, ethanol, propanol, isopropyl alcohol, and the like; and other solvents known in the art. Preferred organic solvents are absolute ethanol or isopropy alcohol.

Except where both $R^5$ and $R^6$ are alkyl, the halomethyl-2-pyridinamine of Formula III is usually used as an acylated derivative, preferably where one of $R^5$ or $R^6$ is $C_2-C_6$ alkanoyl. The term "$C_2-C_6$ alkanoyl" refers to straight or branched chain alkanoyl groups having from 2 to 6 carbon atoms. Examples of $C_2-C_6$ alkanoyl are acetyl, propanoyl, butanoyl, pentanoyl, hexanoyl, and the isomeric forms thereof. Preferred alkanoyl groups are trimethylacetyl or acetyl. After the corresponding alkanoyl derivative of a compound of Formula IV has been formed by the reaction of such an acylated halomethyl-2-pyridinamine derivative with a 2-mercaptobenzimidazole of Formula II, the acyl group can be removed by any of several methods known in the art. A preferred method for removing an alkanoyl group uses refluxing aqueous mineral acid, preferably aqueous hydrochloric acid or sulfuric acid. For those compounds of Formula IV that form acid addition salts, either during the initial reaction or during the removal of an alkanoyl group, the corresponding neutral compounds of Formula IV may be readily obtained by methods known to those skilled in the art. For example, treating an acid addition salt with a suitable base, followed by extraction into a suitable water-immiscible organic solvent, gives the free base form of the compound of Formula IV. Suitable bases for neutralization include alkali metal carbonates, such as lithium, sodium, or potassium carbonate; and tertiary amines, such as triethylamine, tributylamine, N-methylmorpholine, and the like; and other such bases known in the art. Preferred bases include sodium carbonate or potassium carbonate. Suitable water-immiscible organic solvents for extraction include alkanes and cycloalkanes; ethers and cyclic ethers; alkyl alkanoate ethers, such as ethyl acetate and the like; aromatic hydrocarbons; halocarbons, such as chloroform, dichloromethane, ethylene dichloride, and the like; and other solvents known in the art. Preferred water-immiscible organic solvents include ethyl acetate, dichloromethane, and chloroform. Compounds that crystallize spontaneously upon addition of the organic solvent may be collected without completing the extraction procedure.

A second route based on Scheme A is preferred if an appropriate halomethyl-2-pyridinamine of Formula III is not commercially available or easily prepared. Thio intermediates of Formula IV may be prepared by an acid-catalyzed reaction of a 2-mercaptobenzimidazole of Formula II with a hydroxymethyl-2-pyridinamine (Formula III in which Y is OH). Preferred conditions include heating a mixture of compounds of Formulas II and III in a suitable acidic medium. A suitable acidic medium is a chemical substance or mixture of chemical substances that dissolves the compounds of Formulas II and III and is sufficiently acidic to induce the desired reaction, but which does not itself form significant quantities if byproducts by reaction with the compounds of Formulas II and III. Preferred acidic media include mixtures of a hydrogen halide (such as hydrogen chloride or hydrogen bromide) in glacial acetic acid or an aqueous hydrohalic acid (such as hydrochloric or hydrobromic acid) in acetic acid. After the reaction is quenched by pouring the mixture over ice and the mixture is neutralized with a suitable base (such as potassium carbonate), the thio intermediate IV may be isolated and purified by methods known in the art, including recrystallization and chromatography.

The sulfoxide compounds of this invention, Formula I, may be prepared by oxidation of the thio intermediates of Formula IV using methods known to those skilled in the art. Commonly used oxidizing agents include, for example, peracids, such as m-chloroperoxybenzoic acid; peresters; peroxides, such as hydrogen peroxide; sodium metaperiodate; selenium dioxide; manganese dioxide; iodosobenzene; and the like. Preferred conditions for preparing sulfoxides of Formula I include oxidizing intermediates IV with an approximately equimolar quantity of m-chloroperoxybenzoic acid in a suitable organic solvent at temperatures below 0°. Suitable organic solvents for the oxidation include alkanes and cycloalkanes; aromatic hydrocarbons; halocarbons, such as chloroform, dichloromethane, ethylene dichloride, and the like; and other solvents known in the art. A preferred organic solvent is dichloromethane. Oxidization is then quenched by adding dimethylsulfide. The sulfoxides of Formula I may then be isolated and purified by methods known in the art, including recrystallization and chromatography.

Further oxidation of the sulfoxide compounds of Formula I yields corresponding sulfones of Formula V. The sulfones may form in situ during the initial oxidation reaction of thio intermediates of Formula IV or may be prepared by a separate oxidation of isolated sulfoxides of Formula I. The sulfones of Formula V may then be isolated and purified by methods known in the art, including recrystallization and chromatography. Where the sulfones of Formula V are prepared along with sulfoxides of Formula I during the initial oxidation reaction, the preferred method of isolation is chromatography.

Acid addition salts of this invention may be prepared during the course of the reactions (as described above), by ion exchange from those salts using methods known in the art, or by acidification of free bases of the compounds. Base addition salts of this invention by methods known in the art, including those methods disclosed in British Pat. No. 2,137,616.

Although some 2-mercaptobenzimidazoles of Formula II (used as described in Scheme A) are commercially available, they may also be prepared by methods known to those skilled in the art. For example, Scheme B illustrates the preparation of 2-mercaptobenzimidazoles from substituted diaminobenzenes of Formula VI.

SCHEME B

A preferred cyclization method employs an alkali metal alkylxanthate salt of the formula alkyl-O(C=O)S$^-$M+, where M+ represents an alkali metal ion. Such alkylxanthate salts may be preformed by methods known in the art or may be formed in situ by mixing an alkali metal hydroxide (preferably sodium hydroxide) and carbon disulfide in an alcohol (preferably ethanol). Preferred cyclization conditions include heating an aqueous or

SCHEME B

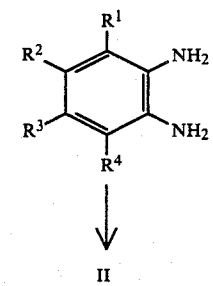

alcoholic mixture of a diaminobenzene of Formula VI with sodium or potassium ethylxanthate at reflux under an inert atmosphere, such as argon.

Halomethyl-2-pyridinamines of Formula III (wherein Y is a halogen, preferably chlorine or bromine) may be prepared by any of various methods known in the art. Scheme C illustrates a preferred preparation of N$^2$-alkanoyl halomethyl-2-pyridinamines (used as described in Scheme A, above).

SCHEME C

Halogenation of N$^2$-alkanoyl methyl-2-pyridinamines of Formula VII using methods known in the art gives the corresponding N$^2$-alkanoyl halomethyl-2-pyridinamines. Preferred halogenation conditions employ a light-induced reaction with an N-halosuccinimide, preferably N-bromosuccinimide, in carbon tetrachloride containing a catalytic amount of 2,2'-azabisisobutyronitrile.

Halomethyl-2-pyridinamines of Formula III may also be prepared from corresponding hydroxymethyl-2-pyridinamines of Formula III (wherein Y is hydroxy) by synthetic methods well known in the art. For example, reaction of such a hydroxymethyl compound with a suitable halogenating reagent in a suitable organic solvent will give the corresponding halomethyl-2-pyridinamine as a hydrochloride

SCHEME C

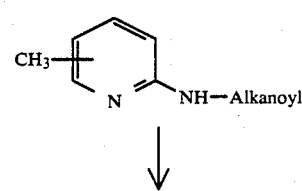

-continued
SCHEME C

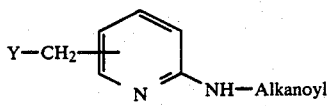
VIII salt. Suitable halogenating agents include thionyl chloride, phosphorus oxychloride, oxalkyl chloride, and the like. Suitable organic solvents for halogenation include alkanes and cycloalkanes; ethers and cyclic ethers; aromatic hydrocarbons; halocarbons, such as chloroform, dichloromethane, ethylene dichloride, and the like: and other solvents known in the art. Preferred organic solvents include dichloromethane and chloroform. A related method involves heating a hydroxymethyl-2-pyridinamine in concentrated hydrochloric or hydrobromic acid at temperatures at 80° to 100° See B. Beilenson and F. M. Hamer, *J. Chem. Soc.*, 98–102 (1942).

Hydroxymethyl-2-pyridinamines of Formula III (wherein Y is a hydroxy) may be prepared by any of various methods known in the art. Scheme D illustrates two preferred preparations of hydroxymethyl-2-pyridinamines (used as described in Scheme A, above). The methods illustrated in Scheme D are best performed on compounds in which both $R^5$ and $R^6$ are $C_1$–$C_6$ alkyl or in which one of $R^5$ or $R^6$ is $C_2$–$C_6$ alkanoyl.

SCHEME D

Hydroxylation of methyl-2-pyridinamines of Formula IX using a trialkyl borate or a trialkylborate and hydrogen peroxide gives the corresponding hydroxymethyl-2-pyridinamines of Formula XI. Preferred

SCHEME D

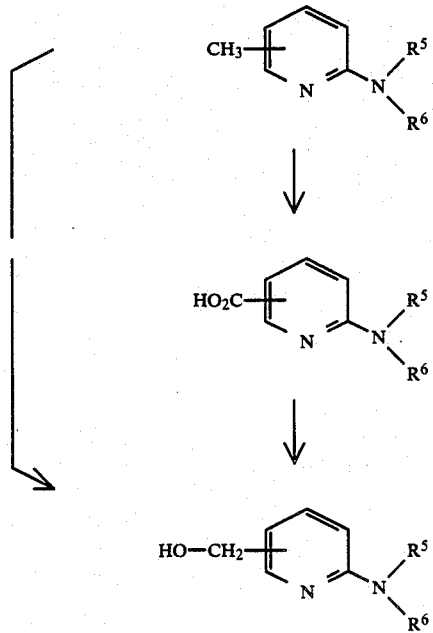

conditions involve an initial deprotonation at the methyl group using a suitable strong base in a suitable organic solvent maintained at temperatures below 0° C. Suitable strong bases are chemical compounds that are sufficiently basic to abstract a proton from the methyl group of a compound of Formula IX so that the subsequent reaction with the trialkyl borate or trialkylborane can take place. Examples of suitable strong bases include alkali metal hydrides, such as sodium hydride and potassium hydride; alkali metal alkyls, such as n-butyllithium and t-butyllithium; and the like. Suitable organic solvents for deprotonation include alkanes and cycloalkanes; ethers and cyclic ethers; aromatic hydrocarbons; and other solvents known in the art. A preferred organic solvent is tetrahydrofuran After deprotonation is effected, a trialkyl borate, preferably trimethyl borate, is added. Subsequent reaction with aqueous hydrogen peroxide gives the hydroxymethyl-2-pyridinamine of Formula XI.

Another preferred hydroxylation method involves an initial oxidation of methyl-2-pyridinamines of Formula IX to carboxylic acids of Formula X using methods known in the art. A preferred oxidation employs potassium permanganate in water heated to about 50° to 80° C. The carboxlic acid may then be reduced to the corresponding hydroxymethyl-2-pyridinamine of Formula XI using reduction methods known in the art. Examples of reduction methods include reaction with lithium aluminum hydride, a borane, and the like. A preferred reduction method employs borane in tetrahydrofuran.

The preferred embodiments of this invention include 3-[(1H-benzimidazol-2-ylsulfinyl)methyl]-2-pyridinamines and 6-[(1H-benzimidazol-2-ylsulfinyl)methyl]-2-pyridinamines of the following general structure:

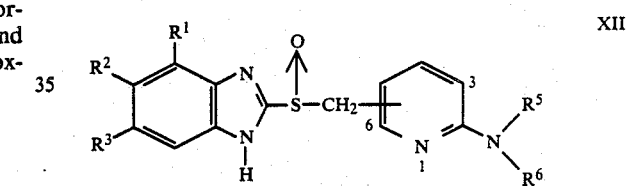
XII or the pharmaceutically acceptable acid addition salts thereof; wherein $R^1$, $R^2$, and $R^3$ are independently hydrogen, $C_1$–$C_6$ alkyl, $C_1$–$C_6$ alkoxy, $C_2$–$C_6$ hydroxyalkyl, $C_1$–$C_4$ fluorinated alkyl, or halogen; and wherein $R^5$ and $R^6$ are independently hydrogen or $C_1$–$C_6$ alkyl.

The most preferred embodiments of this invention include 6-[(1H-benzimidazol-2-ylsulfinyl)methyl]-2-pyridinamines of the following general structure:

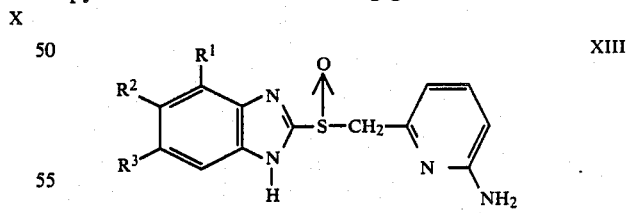
XIII or the pharmaceutically acceptable acid addition salts thereof; wherein $R^1$, $R^2$, and $R^3$ are independently hydrogen, $C_1$–$C_6$ alkyl, $C_1$–$C_6$ alkoxy, $C_2$–$C_6$ hydroxyalkyl, $C_1$–$C_4$ fluorinated alkyl, or halogen.

The compounds of this invention exhibited gastric antisecretory activity in canines, as indicated by inhibition in vitro of $(H^+ + K^+)$-ATPase obtained from canine gastric mucosa and by inhibition in vivo of gastric acid secretion in dogs. The antisecretory activity of the compounds of this invention illustrated in the Examples was tested by the following methods.

Inhibition of ($H^+ + K^+$)-ATPase from Canine Gastric Mucosa

Mongrel dogs weighing 15 to 25 kilograms were fasted for twenty-four hours, with water provided ad libitum. The animals were anesthetized with pentobarbital and the stomachs were removed. Subsequent tissue manipulations and subcellular fractionations were performed at 0° to 4° C. After the stomachs were cut open and rinsed with tap water, the antral and cardiac regions were removed and the remaining tissue was rinsed three times in saline. The glandular mucosa was removed mechanically, chopped finely in a medium containing 10 mM Tris hydrochloride (pH 7.4) and 250 mM sucrose, and homogenized. The homogenate was centrifuged at 20,000xg for twenty minutes and the pellet discarded. The supernatant was then centrifuged at 150,000xg for ninety minutes and the supernatant discarded. The pellet was resuspended in the Tris-HCl/sucrose medium by homogenization. Part (2 ml) of the resultant microsomal suspension was layered onto a step gradient consisting of 9 ml of 15% sucrose above 12 ml of 30% sucrose, each sucrose solution being buffered with 10 mM Tris hydrochloride (pH 7.4) containing 0.01% sodium azide. The microsomes retained at the 15%–30% sucrose interface, after centrifugation at 250,000xg for sixty minutes, were used as the source of ($H^+ + K^+$)-ATPase. Microsomal preparations were lyophilized, a process that assured potassium ion permiability, and stored at $-10°$ until used.

($H^+ + K^+$)-ATPase activity for each test compound was determined, in duplicate, by measuring the release of inorganic phosphate, which was assayed according to the method of J. ChandraRajan and L. Klein. *Anal. Biochem.*, 72, 407–412 (1976). The ($H^+ + K^+$)-ATPase assay medium consisted of 20 mM Mes-Tris (pH 6.0), 5 mM magnesium chloride, 25 mM sucrose, and 4 mM Tris-ATP with or without 20 mM potassium chloride in a total volume of 2 ml. Microsomal suspensions (20 to 60 mcl, containing about 25 mcg protein) were added to the assay medium, without Tris-ATP, and then preincubated with a test compound for thirty minutes at 37°. The assay was initiated by adding Tris-ATP and the mixture was incubated another thirty minutes at 37° A 200-mcl aliquot of the assay mixture was then added to 1.4 ml of a solution consisting of 0.1M sodium acetate (pH 4.0) and 10% sodium dodecylsulfate, followed by the addition of 200 mcl each of 1% ammonium molybdate and 1% ascorbic acid. At least fifteen minutes later, the optical absorbance at 870 nm (which was proportional to inorganic phosphate concentration up to 100 nmoles per tube, as determined by a standard curve) was obtained. Enzyme activity was linear with incubation time.

($H^+ + K^+$)-ATPase activity is represented by the difference between the measured activities in the presence of potassium ion ($K^+$-stimulated) and in the absence of potassium ion (basal). The concentration of a test compound required to inhibit 50% of the ($H^+ + K^+$)-ATPase activity (i.e., the $IC_{50}$) was determined at least in duplicate using linear regression analysis of results obtained for three different compound concentrations ranging from 0.1 mcM to 0.2 mM. If the $IC_{50}$ for a test compound could not be determined for the concentration range tested, percent inhibition of ($H^+ + K^+$)-ATPase was obtained for the compound at 0.1 mM.

Inhibition of Gastric Acid Secretion in Gastric Fistula Beagle Dogs

Adult female beagle dogs weighing 6 to 11 kilograms obtained from Laboratory Research Enterprises (Kalamazoo, Mich.) or from Hazelton Research Animals (Cumberland, Va.) were surgically implanted with a simple Thomas-type gastric cannula. After recovery from surgery, the dogs were trained to stand quietly, fully conscious, in Pavlov-type dog restraining slings and were acclimated to intravenous infusion of histamine dihydrochloride. During the course of these studies, no dog was used more than once a week. All dogs were deprived of food, but not water, for 18 hours prior to each assay. Each dog was initially infused with 0.15M sodium chloride solution at a constant rate of 6.5 mg/hr. The volume of gastric secretions, collected in plastic bottles affixed to the cannula, were measured to the nearest 0.1 ml at 30 minute intervals. One of the following protocols was followed, depending on the route chosen for administration of test compound.

Intravenous dosing: Following a 30-minute basal secretion period, test compounds were administered intravenously (i.v.). At the end of an additional 30 minute period, the saline infusion was replaced with histamine dihydrochloride in saline administered at a rate 15 mcg per kilogram of body weight per hour. Histamine stimulation was maintained for a maximum of four hours during which time gastric secretions were collected every 30 minutes. The pH and titratable acidity were determined for samples from each collection period.

Intragastric dosing: Following a 30-minute basal secretion period, the collection bottles were removed, dosing plugs were inserted, and test compounds were administered intragastrically (i.g.). At the end of a 30-minute drug absorption period, the stomachs were emptied, the collection bottles were reattached, and collections were resumed at 30-minute intervals. Simultaneously, the saline infusion was replaced with a continuous intravenous infusion of histamine dihydrochloride in saline administered for four hours at a rate 15 mcg per kilogram of body weight per hour.

Intraduodenal dosing: Dogs were also equipped with duodenal cannulas for intraduodenal (i.d.) administration of test compounds. Dosing was otherwise performed as described for intragastric dosing.

Data from each protocol were analyzed for three gastric sample variables: volume of gastric juice, acid concentration, and total acid output. Percent inhibition for each four-hour experimental period was determined for each parameter by comparison with 3 to 4 controls in which only food was given. Estimates of $ED_{50}$'s were determined from dose response curves.

By virtue of their gastric antisecretory activity, the compounds of Formula I are useful in treating ulcers in mammals. A physician or veterinarian of ordinary skill can readily determine whether a subject has ulcers. Regardless of the route of administration selected, the compounds of the present invention are formulated into pharmaceutically acceptable dosage forms by conventional methods known to those skilled in the art. The compounds may be formulated using pharmacologically acceptable acid addition or base addition salts. Moreover, the compounds or their salts may be used in a suitable hydrated form.

The compounds can be administered in such oral dosage forms as tablets, capsules, pills, powders, granules, elixirs, or syrups. The compounds may also be administered intravascularly, intraperitoneally, subcutaneously, or intramuscularly, using forms known to the pharmaceutical art. In general, the preferred form of administration is oral. For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For example, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol, and the like, or various combinations thereof; for oral administration in liquid form, the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium actate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, active drug components may be combined with a suitable carrier such as water, saline, aqueous dextrose, and the like.

By whatever route of administration selected, an effective but non-toxic quantity of the compound is employed in treatment. The dosage regimen for preventing or treating ulcers with the compounds of this invention is selected in accordance with a variety of factors, including the type, age, weight, sex, and medical condition of the patient; the severity of the condition; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention may be in the range of about 1.0 mcg/kg to 500 mg/kg, preferably in the range of about 10 to 100 mg/kg orally or about 1.0 to 20 mg/kg intravenously.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

DESCRIPTION OF THE PREFERRED EMBODIMENTS

EXAMPLE 1

3-[(1H-benzimidazol-2-ylthio)methyl]-2-pyridinamine hemihydrate

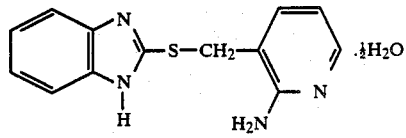

A mixture of 9.6 g (63 mmole) of 2-mercaptobenzimidazole and 7.7 g (62 mmole) of 3-hydroxymethyl-2-pyridinamine was dissolved in 60 ml of 48% aqueous hydrobromic acid and 60 ml of acetic acid and heated to reflux. After being cooled to room temperature, the mixture was poured into water and made alkaline with potassium carbonate. The oil that separated solidified upon addition of diethyl ether to the aqueous mixture. The solid was collected by filtration, washed with portions of diethyl ether and water, and air dried to yield 12.4 g of the title compound as an analytically pure hemihydrate. Structure assignment was supported by the nmr and infrared spectra and by elemental analysis. Analysis. Calcd. for $C_{13}H_{12}N_4S\cdot\frac{1}{2}H_2O$: C, 58.84; H, 4.93; N, 21.11; S, 12.08. Found: C, 59.06; H, 4.48; N, 20.82; S, 12.16.

EXAMPLE 2

3-[(1H-benzimidazol-2-ylsulfonyl)methyl]-2-pyridinamine

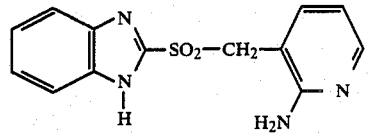

A suspension of 4.0 g (15 mmole) of 3-[(1H-benzimidazol-2-ylthio)methyl]-2-pyridinamine hemihydrate (see Example 1) in 50 ml of dichloromethane was cooled in an ice bath. A solution of 3.0 g (15 mmole) of ca. 85% m-chloroperbenzoic acid in the minimum amount of dichloromethane needed to form a solution was then added dropwise with stirring. After addition was complete, another 3.0 g of ca. 85% m-chloroperbenzoic acid was added. The reaction was quenched with 10 drops of dimethylsulfide. The mixture was washed with saturated aqueous sodium bicarbonate. The organic phase was concentrated in vacuo and chromatographed on silica gel (using ethanol-dichloromethane-triethylamine as eluent). Initial fractions yielded 249 mg of the title sulfone. Structure assignment was supported by the nmr and infrared spectra and by elemental analysis.

Analysis. Calcd. for $C_{12}H_{12}N_4SO_2$: C, 54.15; H, 4.19; N, 19.43. Found: C, 53.79; H, 4.09; N, 19.29.

EXAMPLE 3

3-[(1H-benzimidazol-2-ylsulfinyl)methyl]-2-pyridinamine hydrate

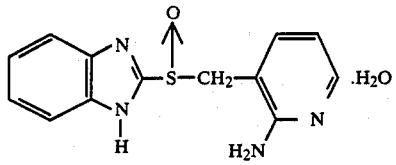

Later fractions from the chromatographic separation of Example 2 yielded 653 mg of the title sulfoxide. Structure assignment was supported by the nmr and infrared spectra and by elemental analysis.

Analysis. Calcd. for $C_{13}H_{12}N_4SO \cdot H_2O$: C, 53.77; H, 4.16; N, 12.29; S, 11.04. Found: C, 53.59; H, 4.34; N, 18.93; S, 11.26.

EXAMPLE 4

3-[(1H-benzimidazol-2-ylthio)methyl]-N,N-dimethyl-2-pyridinamine

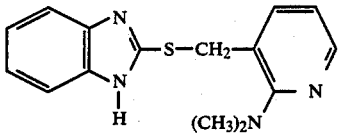

To a cold (ca. −78°) solution of 2.9 g (21 mmole) of 3-methyl-2-(N,N-dimethylamino)pyridine in 35 ml of tetrahydrofuran was added dropwise 15 ml (23 mmole) of 1.55M butyllithium in hexane. The mixture was stirred at 0° for four hours and then recooled to ca. −78°.

Trimethyl borate (2.65 ml, ca. 23 mmole) was added dropwise and the mixture was stirred at 0°. After one hour 2.9 ml of 30% hydrogen peroxide was added and the mixture was stirred at 25°. After another hour the reaction mixture was poured into water and extracted with several portions of diethyl ether. The combined ether extracts were dried over magnesium sulfate, filtered, and concentrated in vacuo to an oil. Chromatography on silica gel (using ethanol-toluene as eluent) yielded 600 mg of 3-hydroxymethyl-2-(N,N-dimethylamino)pyridine, as confirmed by the nmr and infrared spectra. Using the method of Example 1 with 3-hydroxymethyl-2-(N,N-dimethylamino)pyridinamine instead of 3-hydroxymethyl-2-pyridinamine yielded the title compound, which was used in subsequent reactions without further purification. Structure assignment was supported by the nmr and infrared spectra.

EXAMPLE 5

3-[(1H-benzimidazol-2-ylsulfinyl)methyl]-N,N-dimethyl-2-pyridinamine ⅓ hydrate

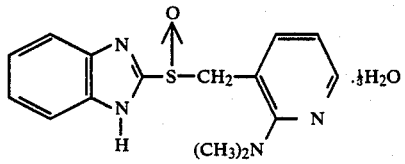

The title compound was prepared by the method of Example 2 using 1.5 g of 3-[(1H-benzimidazol-2-ylsulfinyl)methyl]-N,N-dimethyl-2-pyridinamine (see Example 4) instead of 3-[(1H-benzimidazol-2-ylthio)methyl]-2-pyridinamine hemihydrate and using chloroform as solvent instead of dichloromethane. Structure assignment was supported by the nmr and infrared spectra and by elemental analysis.

Analysis. Calcd. for $C_{15}H_{16}N_4OS \cdot \frac{1}{3}H_2O$: C, 58.84; H, 5.48; N, 18.29; S, 10.44. Found: C, 59.24; H, 5.31; N, 18.10; S, 10.05.

EXAMPLE 6

6-[(1H-benzimidazol-2-ylthio)methyl]-2-pyridinamine hemihydrate

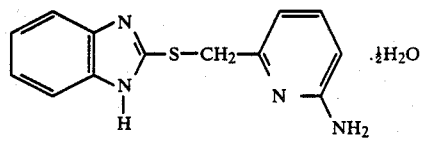

To a cold (ca. 0°) solution of 86.4 g (0.88 mole) of 2-amino-6-methylpyridine and 101 g (0.96 mole) of triethylamine in 1.0 liter of dichloromethane was added dropwise a solution of 106.1 g (0.88 mole) of trimethylacetyl chloride in 100 ml of dichloromethane. After stirring an hour after addition was completed, the mixture was poured into water and the layers separated. The aqueous layer was extracted with dichloromethane. The organic layers were combined and washed with water, dried over magnesium sulfate, filtered, and concentrated in vacuo to an oil that crystallized upon standing. The solid was triturated with hexane and collected by filtration, giving 115 g of 2-(trimethylacetamido)-6-methylpyridine. A 22.6 g (0.12 mmole) portion of the amide derivative was suspended in 250 ml of carbon tetrachloride containing 22.9 g (0.12 mmole) of N-bromosuccinimide and 100 mg of 2,2'-azabisisobutyronitrile. The mixture was heated at reflux under a sun lamp for one hour, after which insolubles were removed by filtration. The filtrate was concentrated in vacuo to an oil consisting of a mixture of the 6-bromomethyl-2-(trimethylacetamido)pyridine and 6-dibromoethyl-2-(trimethylacetamido)pyridine derivatives. The crude mixture was heated at reflux for fifteen minutes with 11.7 g (78 mmole) of 2-mercaptobenzimidazole in 300 ml of isopropyl alcohol. Upon cooling, a precipitate formed and was collected and washed with portions of isopropyl alcohol and diethyl ether. The trimethylacetyl group was removed by heating at reflux for four hours in 300 ml of 10% aqueous hydrochloric acid. After cooling, the mixture was concentrated in vacuo to an oil. The oil was dissolved in water and made alkaline with aqueous potassium carbonate. The oil that separated solidified upon addition of dichloromethane to the aqueous mixture. The solid was collected by filtration, washed with portions of water and dichloromethane, and air dried to yield 9.6 g of the title compound as an analytically pure hemihydrate. (An additional 2.5 g of the title compound was isolated from the dichloromethane washes.) Structure assignment was supported by the nmr and infrared spectra and by elemental analysis.

Analysis. Calcd. for $C_{13}H_{12}N_4S \cdot \frac{1}{2}H_2O$: C, 58.84; H, 4.93; N, 21.11; S, 12.08. Found: C, 59.03; H, 4.40; N, 20.90; S, 12.30.

EXAMPLE 7

6-[(1H-benzimidazol-2-ylsulfinyl)methyl]-2-pyridinamine

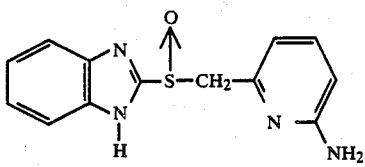

A suspension of 5.0 g (18.8 mmole) of 6-[(1H-benzimidazol-2-ylthio)methyl]-2-pyridinamine hemihydrate (see Example 6) in 250 ml of chloroform was cooled to −5°. A solution of 4.2 g (20 mmole) of ca. 85% m-chloroperbenzoic acid in chloroform was added dropwise with stirring. After an additional fifteen minutes, the reaction was quenched with several drops of dimethylsulfide and concentrated in vacuo. The residue was triturated with diethyl ether, filtered, and washed with diethyl ether, yielding 2.6 g of the title compound. Structure assignment was supported by the nmr and infrared spectra and by elemental analysis.

Analysis. Calcd. for $C_{13}H_{12}N_4SO$: C, 57.33; H, 4.44; N, 20.57; S, 11.77. Found: C, 57.04; H, 4.42; N, 20.50; S, 11.87.

EXAMPLE 8

6-[[(4-methyl-1H-benzimidazol-2-yl)thio]methyl]-2-pyridinamine hemihydrate

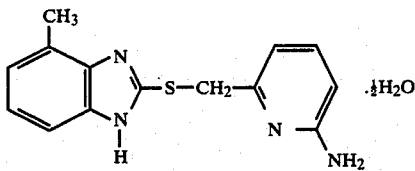

A solution of 20 g (0.13 mole) of 2-methyl-6-nitroaniline in 22.9 ml of concentrated aqueous hydrochloric acid, 200 ml of tetrahydrofuran, and 350 ml of methanol was hydrogenated at room temperature using 25 p.s.i. of hydrogen gas over 2.0 g of 5% palladium on carbon. The mixture was filtered and the filtrate was concentrated in vacuo. The residue was dissolved in 150 ml of ethanol and neutralized with 17.2 g (0.26 mole) of potassium hydroxide dissolved in 30 ml of water. Potassium ethylxanthate (23 g, 0.155 mole) was added and the mixture was heated at reflux for 18 hours. Upon cooling, a solid was collected, washed with water, and air dried to yield 6.2 g of 2-mercapto-4-methylbenzimidazole, as confirmed by the nmr and infrared spectra. The title compound (1.5 g) was prepared by the method of Example 6 using 1.6 g of 2-mercapto-4-methylbenzimidazole instead of 2-mercaptobenzimidazole. Structure assignment was supported by the nmr and infrared spectra and by elemental analysis.

Analysis. Calcd. for $C_{14}H_{14}N_4S\cdot\frac{1}{2}H_2O$: C, 60.19; H, 5.01; N, 20.05; S, 11.45. Found: C, 60.49; H, 5.03; N, 20.41; S, 11.76.

EXAMPLE 9

6-[[(4-methyl-1H-benzimidazol-2-yl)-sulfinyl]methyl]-2-pyridinamine

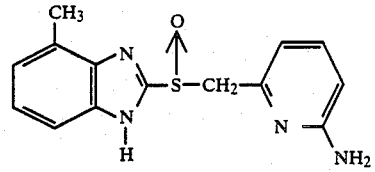

The title compound (450 mg) was prepared by the method of Example 7 using 600 mg (2.2 mmole) of 6-[[(4-methyl-1H-benzimidazol-2-yl)thio]methyl]-2-pyridinamine (see Example 8) instead of 6-[(1H-benzimidazol-2-ylthio)methyl]-2-pyridinamine. Structure assignment was supported by the nmr and infrared spectra and by elemental analysis.

Analysis. Calcd. for $C_{14}H_{14}N_4SO$: C, 58.72; H, 4.93; N, 19.57; S, 11.20. Found: C, 58.70; H, 4.86; N, 19.60; S, 10.88.

EXAMPLE 10

6-[[(5-methyl-1H-benzimidazol-2-yl)thio]methyl]-2-pyridinamine hemihydrate

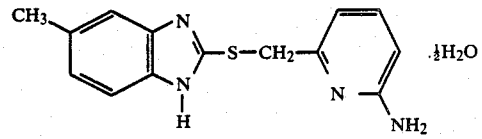

A mixture of 12.2 g (0.1 mole) of 3,4-diaminotoluene, 35 ml of carbon disulfide, and 4.0 g (0.1 mole) of sodium hydroxide was heated at reflux in 350 ml of ethanol. After 2.5 hours the mixture was concentrated in vacuo. The residue was suspended in 200 ml of 4% aqueous hydrochloric acid, and the product was collected by filtration, washed sequentially with water and diethyl ether, and air dried to yield 12.2 g of 2-mercapto-5-methylbenzimidazole, as confirmed by the nmr and infrared spectra. The title compound (2.0 g) was prepared by the method of Example 6 using 1.6 g (9.7 mmole) of 2-mercapto-5-methylbenzimidazole instead of 2-mercaptobenzimidazole. Structure assignment was supported by the nmr and infrared spectra and by elemental analysis.

Analysis. Calcd. for $C_{14}H_{14}N_4S$: C, 60.19; H, 5.01; N, 20.05; S, 11.47. Found: C, 59.80; H, 5.05; N, 20.00; S, 11.17.

EXAMPLE 11

6-[[(5-methyl-1H-benzimidazol-2-yl)sulfinyl]methyl]-2-pyridinamine

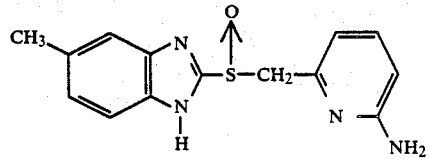

The title compound (240 mg) was prepared by the method of Example 7 using 1.0 g (3.7 mmole) of 6-[[(5- methyl-1H-benzimidazol-2-yl)thio]methyl]-2-pyridinamine (see Example 10) instead of 6-[(1H-benzimidazol-2-ylthio)methyl]-2-pyridinamine. Structure assignment was supported by the nmr and infrared spectra and by elemental analysis.

Analysis. Calcd. for $C_{14}H_{14}N_4SO$: C, 58.72; H, 4.93; N, 19.57; S, 11.20. Found: C, 58.62; H, 4.91; N, 19.60; S, 10.99.

EXAMPLE 12

6-[[(5-methoxy-1H-benzimidazol-2-yl)thio]methyl]-2-pyridinamine

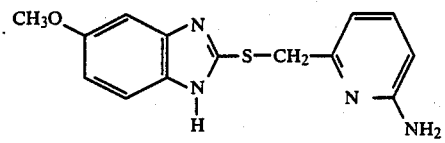

The title compound was prepared by the method of Example 6 using 7.0 g of 2-mercapto-5-methoxybenzimidazole instead of 2-mercaptobenzimidazole. Structure assignment was supported by the nmr spectrum.

EXAMPLE 13

6-[[(5-methoxy-1H-benzimidazol-2-yl)thio]methyl]-2-pyridinamine

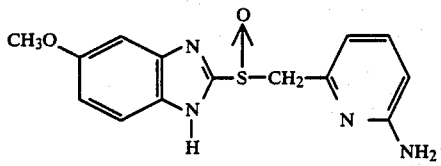

The title compound (940 mg) was prepared by the method of Example 7 using 4.67 g (16.3 mmole) of 6-[[(5-methoxy-1H-benzimidazol-2-yl)thio]methyl]-2-pyridinamine (see Example 12) instead of 6-[(1H-benzimidazol-2-ylthio)methyl]-2-pyridinamine. Structure assignment was supported by the nmr and infrared spectra and by elemental analysis.

Analysis. Calcd. for $C_{14}H_{14}N_4SO$: C, 55.62; H, 4.67; N, 18.53; S, 10.60. Found: C, 55.52; H, 4.59; N, 17.86; S, 10.35.

EXAMPLE 14

6-[[(5-chloro-1H-benzimidazol-2-yl)thio]methyl]-2-pyridinamine

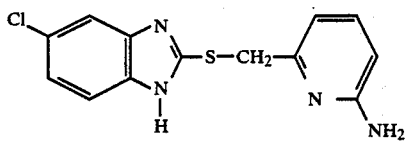

A solution of 20 g (0.12 mole) of 3-chloro-6-nitroaniline in 350 ml of methanol was hydrogenated over 5% palladium on carbon to yield 24.9 g of the corresponding diamino compound. Reaction of the diamino compound with potassium ethylxanthate using the method described in Example 8 yielded 19 g of 5-chloro-2-mercaptobenzimidazole, as confirmed by elemental analysis. The title compound (1.8 g) was prepared by the method of Example 6 using 3.6 g (19 mmole) of 5-chloro-2-mercaptobenzimidazole instead of 2-mercaptobenzimidazole. Structure assignment was supported by the nmr and infrared spectra.

EXAMPLE 15

6-[[(5-chloro-1H-benzimidazol-2-yl)sulfinyl]methyl]-2-pyridinamine

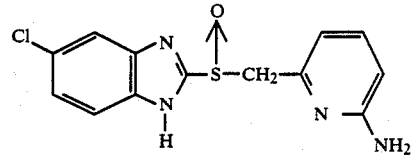

The title compound (250 mg) was prepared by the method of Example 7 using 1.5 g (5.2 mmole) of 6-[[(5-chloro-1H-benzimidazol-2-yl)thio]methyl]-2-pyridinamine (see Example 14) instead of 6-[(1H-benzimidazol-2-ylthio)methyl]-2-pyridinamine. Structure assignment was supported by the nmr spectrum and by elemental analysis.

Analysis. Calcd. for $C_{13}H_{11}N_4ClSO$: C, 50.90; H, 3.61; N, 18.26, S, 10.45; Cl, 11.56. Found: C, 50.97; H, 3.60; N, 18.45; S, 10.47; Cl, 11.74.

EXAMPLE 16

6-[[[5-(trifluoromethyl)-1H-benzimidazol-2-yl]thio]methyl]-2-pyridinamine

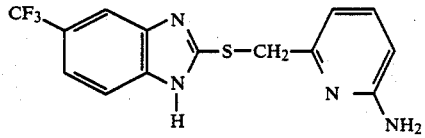

A solution of 50 g (0.24 mole) of 4-(trifluoromethyl)-2-nitroaniline in 500 ml of ethanol was hydrogenated over 10% palladium on carbon to yield 21.0 g of the corresponding diamino compound. Reaction of 20.0 g of the diamino compound with carbon disulfide using the method described in Example 10 yielded 22.9 g of 5-(trifluoromethyl)-2-mercaptobenzimidazole, as confirmed by elemental analysis. The title compound (1.5 g) was prepared by the method of Example 6 using 5.7 g (26 mmole) of 5-(trifluoromethyl)-2-mercaptobenzimidazole instead of 2-mercaptobenzimidazole. Structure assignment was supported by the nmr and infrared spectra.

EXAMPLE 17

6-[[[5-(trifluoromethyl)-1H-benzimidazol-2-yl]sulfinyl]methyl]-2-pyridinamine

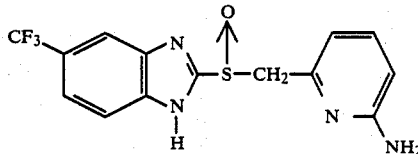

The title compound (900 mg) was prepared by the method of Example 7 using 1.5 g (4.6 mmole) of 6-[[[5-trifluoromethyl)-1H-benzimidazol-2-yl]thio]methyl]-2-pyridinamine (see Example 16) instead of 6-[(1H-benzimidazol-2-ylthio)methyl]-2-pyridinamine. Structure assignment was supported by the nmr and infrared spectra and by elemental analysis.

Analysis. Calcd. for $C_{14}H_{11}N_4F_3SO$: C, 49.41; H, 3.26; N, 16.46; S, 9.42. Found: C, 49.42; H, 3.29; N, 16.30; S, 9.49.

EXAMPLE 18

6-[[(5-ethoxy-1H-benzimidazol-2-yl)thio]methyl]-2-pyridinamine

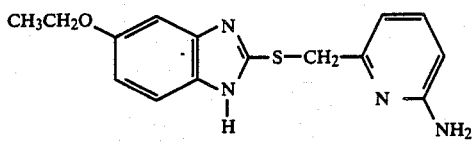

A solution of 51.3 g (0.28 mole) of 4-ethoxy-2-nitroaniline in methanol was hydrogenated over 5% palladium on carbon to yield 63.4 g of the corresponding diamino compound. Reaction of the diamino compound with potassium ethylxanthate using the method described in Example 8 yielded 43.4 g of 5-ethoxy-2-mercaptobenzimidazole, as confirmed by the nmr and infrared spectra. The title compound (1.0 g) was prepared by the method of Example 6 using 3.7 g of 5-ethoxy-2-mercaptobenzimidazole instead of 2-mercaptobenzimidazole. The title compound was used in subsequent reactions without further characterization.

EXAMPLE 19

6-[[(5-ethoxy-1H-benzimidazol-2-yl)sulfinyl]methyl]-2-pyridinamine

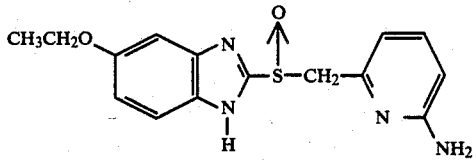

The title compound (700 mg) was prepared by the method of Example 7 using 900 mg (3.0 mmole) of 6-[[(5-ethoxy-1H-benzimidazol-2-yl)thio]methyl]-2-pyridinamine (see Example 18) instead of 6-[(1H-benzimidazol-2-ylthio]methyl]-2-pyridinamine. Structure assignment was supported by the nmr and infrared spectra and by elemental analysis.

Analysis. Calcd. for $C_{15}H_{16}N_4SO_2$: C, 56.95; H, 5.10; N, 17.71; S, 10.14. Found: C, 56.67; H, 4.99; N, 17.48; S, 10.27.

EXAMPLE 20

6-[[(5,6-dimethoxy-1H-benzimidazol-2-yl)thio]methyl]-2-pyridinamine ¾ hydrate

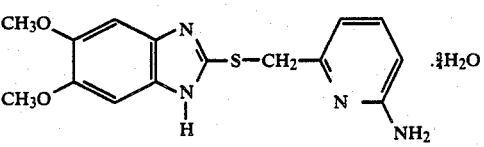

A solution of 62.2 g (0.31 mole) of 3,4-dimethoxy-6-nitroaniline in tetrahydrofuran was hydrogenated with Raney nickel to yield 52.7 g of the corresponding diamino compound. Reaction of the diamino compound with potassium ethylxanthate using the method described in Example 8 yielded 59 g of 5,6-dimethoxy-2-mercaptobenzimidazole as confirmed by the nmr and infrared spectra. The title compound (1.9 g) was prepared by the method of Example 6 using 4.3 g of 5,6-dimethoxy-2-mercaptobenzimidazole instead of 2-mercaptobenzimidazole. Structure assignment was supported by the nmr and infrared spectra and by elemental analysis.

Analysis. Calcd. for $C_{15}H_{16}N_4SO.3/4H_2O$: C, 54.61; H, 5.30; N, 16.98; S, 9.70. Found: C, 54.75; H, 5.13; N, 17.08; S, 9.72.

EXAMPLE 21

6-[[(5,6-dimethoxy-1H-benzimidazol-2-yl)sulfinyl]methyl]-2-pyridinamine ¼ hydrate

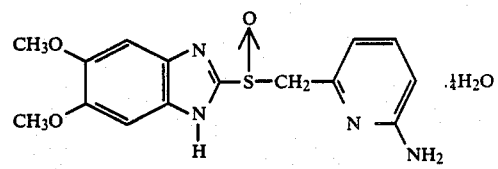

The title compound (600 mg) was prepared by the method of Example 7 using 1.6 g (5.0 mmole) of 6-[[(5,6-dimethoxy-1H-benzimidazol-2-yl)thio]methyl]-2-pyridinamine (see Example 20) instead of 6-[(1H-benzimidazol-2-ylthio)methyl]-2-pyridinamine. Structure assignment was supported by the nmr spectrum and by elemental analysis.

Analysis. Calcd. for $C_{15}H_{16}N_4SO_3.1/4H_2O$: C, 53.48; H, 4.90; N, 16.63; S, 9.52. Found: C, 53.54; H, 4.57; N, 16.45; S, 9.79.

EXAMPLE 22

6-[[(5,6-dimethyl-1H-benzimidazol-2-yl)thio]methyl]-2-pyridinamine

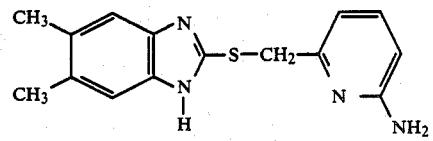

Reaction of 30 g (0.22 mole) of 4,5-dimethyl-1,2-phenylenediamine with potassium ethylxanthate using the method described in Example 8 yielded 19 g of 5,6-dimethyl-2-mercaptobenzimidazole, as confirmed by the nmr and infrared spectra and by elemental analysis. The title compound (3.0 g) was prepared by the method of Example 6 using 3.5 g of 5,6-dimethyl-2-mercaptobenzimidazole instead of 2-mercaptobenzimidazole. Structure assignment was supported by the nmr spectrum.

EXAMPLE 23

6-[[(5,6-dimethyl-1H-benzimidazol-2-yl)sulfinyl]methyl]-2-pyridinamine

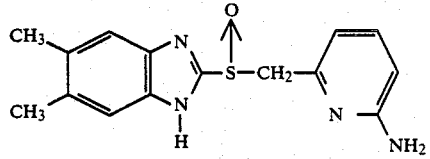

The title compound was prepared by the method of Example 7 using 1.5 g (5.3 mmole) of 6-[[(5,6-dimethyl-1H-benzimidazol-2-yl)thio]methyl]-2-pyridinamine (see Example 22) instead of 6-[(1H-benzimidazol-2-ylthio)methyl]-2-pyridinamine. Structure assignment was supported by the nmr spectrum and by elemental analysis.

Analysis. Calcd. for $C_{15}H_{16}N_4SO$: C, 59.98; H, 5.37; N, 18.65; S, 10.67. Found: C, 59.67; H, 5.20; N, 18.83; S, 10.87.

EXAMPLE 24

6-[[(4,6-dimethyl-1H-benzimidazol-2-yl)thio]methyl]-2-pyridinamine

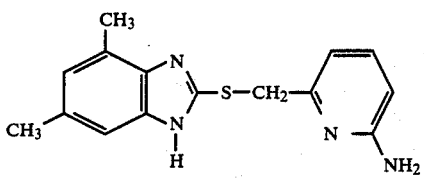

A solution of 5 g (0.03 mole) of 2,4-dimethyl-6-nitroaniline in methanol was hydrogenated over 5% palladium on carbon to yield 4.0 g of the corresponding diamino compound. Reaction of the diamino compound with potassium ethylxanthate using the method described in Example 8 yielded 4.9 g of 4,6-dimethyl-2-mercaptobenzimidazole, as confirmed by the nmr and infrared spectra and by elemental analysis. The title compound (1.5 g) was prepared by the method of Example 6 using 3.5 g (20 mmole) of 4,6-dimethyl-2-mercaptobenzimidazole instead of 2-mercaptobenzimidazole. Structure assignment was supported by the nmr spectrum.

EXAMPLE 25

6-[[(4,6-dimethyl-1H-benzimidazol-2-yl)sulfinyl]methyl]-2-pyridinamine

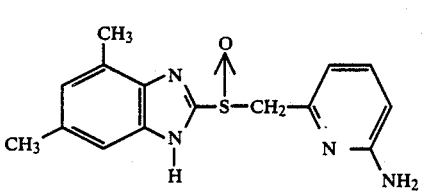

The title compound was prepared by the method of Example 7 using 1.0 g (3.5 mmole) of 6-[[(4,6-dimethyl-1H-benzimidazol-2-yl)thio]methyl]-2-pyridinamine (see Example 24) instead of 6-[(1H-benzimidazol-2-ylthio)methyl]-2-pyridinamine. Structure assignment was supported by the nmr and infrared spectra and by elemental analysis.

Analysis. Calcd. for $C_{15}H_{16}N_4SO$: C, 59.98; H, 5.37; N, 18.65; S, 10.67. Found: C, 59.60; H, 5.32; N, 18.47; S, 10.75.

EXAMPLE 26

6-[[[5-(hydroxymethyl)-1H-benzimidazol-2-yl]thio]methyl]-2-pyridinamine

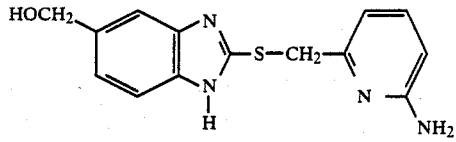

The title compound (600 mg) was prepared by the method of Example 6 using 2.7 g of 5-hydroxymethyl-2-mercaptobenzimidazole instead of 2-mercaptobenzimidazole. Structure assignment was supported by the nmr spectrum.

EXAMPLE 27

6-[[[5-(hydroxymethyl)-1H-benzimidazol-2-yl]sulfinyl]methyl]-2-pyridinamine ¼ hydrate

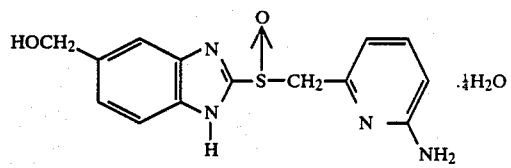

The title compound was prepared by the method of Example 7 using 350 mg of 6-[[[5-(hydroxymethyl)-1H-benzimidazol-2-yl]thio]methyl]-2-pyridinamine (see Example 26) instead of 6-[(1H-benzimidazol-2-ylthio)methyl]-2-pyridinamine. Structure assignment was supported by the nmr and infrared spectra and by elemental analysis.

Analysis. Calcd. for $C_{14}H_{14}N_4SO_2 \cdot 1/4H_2O$: C, 54.80; H, 4.60; N, 18.25; S, 10.44. Found: C, 54.85; H, 4.70; N, 18.01; S, 10.26.

EXAMPLE 28

6-[(1H-benzimidazol-2-ylthio)methyl]-N-(2,2-dimethylpropyl)-2-pyridinamine

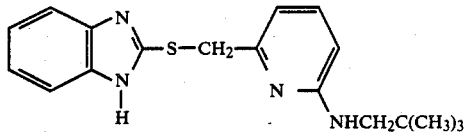

A suspension of 40 g (0.21 mole) of 2-(trimethylacetamido)-6-methylpyridine (prepared as described in Example 6) in 500 ml of water was heated to 70°. Potassium permanganate (65 g, 420 mmole) was added in eight portions over four hours and the mixture was then heated at 90°. After 18 hours the mixture was filtered hot. The filtrate was concentrated in vacuo to about 50 ml and adjusted to about pH 3 with concentrated hydrochloric acid. The resultant precipitate was collected, washed with water, and dried in vacuo to yield 7.5 g of the 6-carboxylic acid derivative. To a suspension of 7.0 g of the carboxylic acid derivative in 50 ml of cold (ca. 0°) tetrahydrofuran was added dropwise 85 ml (ca. 85 mmole) of 1M borane in tetrahydrofuran. The mixture was allowed to stir at room temperature for two hours and at 50° for another 18 hours. After the mixture was allowed to cool, the reaction was quenched with water. The mixture made basic with 10% aqueous sodium hydroxide and extracted with several portions of ethyl acetate. The combined organic layers were dried over magnesium sulfate, filtered, and concentrated in vacuo to an oil. Chromatography on silica gel (using ethanol-dichloromethane as eluent) yielded 1.3 g of 6-hydroxymethyl-N-(2,2-dimethylpropyl)-2-pyridinamine, as confirmed by the nmr and infrared spectra. The title compound (1.9 g) was prepared by the method of Example 1 using 1.3 g (6.7 mmole) of 6-hydroxymethyl-N-(2,2-dimethylpropyl)-2-pyridinamine instead of 3-hydroxymethyl-2-pyridinamine. Structure assignment was supported by the nmr spectrum.

EXAMPLE 29

6-[(1H-benzimidazol-2-ylsulfinyl)methyl]-N-(2,2-dimethylpropyl)-2-pyridinamine ¼ hydrate

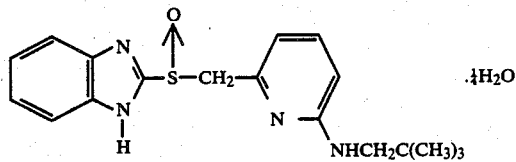

The title compound (100 mg) was prepared by the method of Example 7 using 1.52 g (4.65 mole) of 6-[(1H-benzimidazol-2-ylthio)methyl]-N-(2,2-dimethylpropyl)-2-pyridinamine (see Example 28) instead of 6-[(1H-benzimidazol-2-ylthio)methyl]-2-pyridinamine. Structure assignment was supported by the nmr and infrared spectra and by elemental analysis.

Analysis. Calcd. for $C_{18}H_{22}N_4SO.1/4H_2O$: C, 62.31; H, 6.48; N, 16.15; S, 9.24. Found: C, 62.19; H, 6.47; N, 15.76; S, 9.09.

EXAMPLE 30

6-[(1H-benzimidazol-2-ylthio)methyl]-N-ethyl-2-pyridinamine

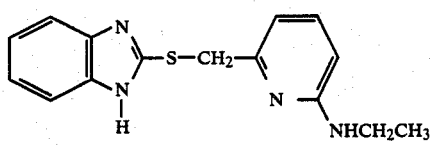

The title compound (2.1 g) was prepared by the method of Example 28 using 45 g (0.30 mole) of 2-acetamido-6-methylpyridine (prepared from 2-amino-6-methylpyridine as described in Example 6 using acetyl chloride instead of trimethylacetyl chloride) instead of 2-(trimethylacetamido)-6-methylpyridine. Structure assignment was supported by the nmr and infrared spectra.

EXAMPLE 31

6-[(1H-benzimidazol-2-ylsulfinyl)methyl]-N-ethyl-2-pyridinamine

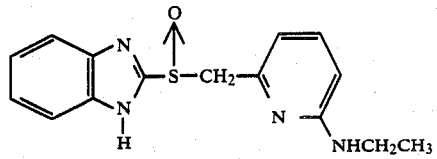

The title compound was prepared by the method of Example 7 using 2.0 g (7.03 mmole) of 6-[(1H-benzimidazol-2-ylthio)methyl]-N-ethyl-2-pyridinamine (see Example 30) instead of 6-[(1H-benzimidazol-2-ylthio)methyl]-2-pyridinamine. Structure assignment was supported by the nmr and infrared spectra and by elemental analysis.

Analysis. Calcd. for $C_{15}H_{16}N_4SO$: C, 59.98; H, 5.37; N, 18.65; S, 10.67. Found: C, 60.07; H, 5.37; N, 18.45; S, 10.61.

EXAMPLE 32

5-[(1H-benzimidazol-2-ylthio)methyl]-2-pyridinamine ¼ hydrate

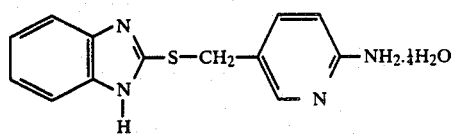

The title compound was prepared by the general method described in Example 6 using 2-amino-5-methylpyridine instead of 2-amino-6-methylpyridine. The crystalline solid was collected and washed with portions of water and diethyl ether to yield 1.8 g of the title compound. Structure assignment was supported by the nmr and infrared spectra and by elemental analysis.

Analysis. Calcd. for $C_{13}H_{12}N_4S.1/4H_2O$: C, 59.86; H, 4.83; N, 21.48; S, 12.29. Found: C, 59.91; H, 4.67; N, 21.86; S, 12.45.

EXAMPLE 33

5-[(1H-benzimidazol-2-ylsulfinyl)methyl]-2-pyridinamine ¼ hydrate

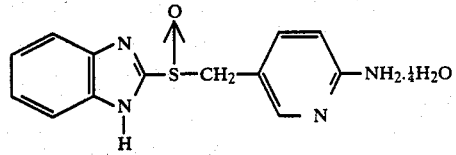

The title compound was prepared by the method of Example 7 using 1.0 g (3.9 mmole) of 5-[(1H-benzimidazol-2-ylthio)methyl]-2-pyridinamine (see Example 32) instead of 6-[(1H-benzimidazol-2-ylthio)methyl]-2-pyridinamine. Structure assignment was supported by the nmr and infrared spectra and by elemental analysis.

Analysis. Calcd. for $C_{13}H_{12}N_4SO.1/4H_2O$: C, 56.40; H, 4.55; N, 20.24; S, 11.58. Found: C, 56.35; H, 4.46; N, 20.25; S, 11.66.

EXAMPLE 34

Table of Pharmacological Test Results

| Compound [Product of Example No.] | $(H^+ + K^+)$-ATPase $IC_{50}$ (mcM) | Gastric-Fistula Beagle % Inhibition (3 mg/kg dose) |
|---|---|---|
| 3 | 100 | 41 i.v. |
| 5 | 8.6 | 15 i.d. |
| 7 | 2.5 | 59 i.d. |
| 9 | 2.2 | |
| 11 | 1.68 | |
| 13 | 4.5 | 46 i.v. |
| 15 | 6.9 | |
| 17 | 6.95 | |
| 19 | 3.1 | |
| 21 | 23.7 | |
| 23 | 0.72 | |
| 25 | 1.8 | |
| 27 | 9.5 | |
| 29 | 9.1 | |
| 31 | 20.0 | 58 i.d. |
| 33 | 34.8 | |

What is claimed is:

1. A compound of the formula:

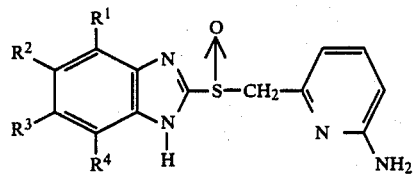

or a pharmaceutically acceptable addition salt thereof; wherein $R^1$, $R^2$, $R_3$, and $R_4$ are independently:
 (a) hydrogen;
 (b) $C_1$-$C_6$ alkyl;
 (c) $C_1$-$C_6$ alkoxyl;
 (d) $C_1$-$C_6$ hydroxyalkyl;
 (e) $C_1$-$C_4$ fluorinated alkyl; or
 (f) halogen.

2. A compound according to claim 1 selected from the group consisting of:
 6-[(1H-benzimidazol-2-ylsulfinyl)methyl]-2-pyridinamine,
 6-[[(4-methyl-1H-benzimidazol-2-yl)sulfinyl]methyl]-2-pyridinamine,
 6-[[(5-methyl-1H-benzimidazol-2-yl)sulfinyl]methyl]-2-pyridinamine,
 6-[[(5-chloro-1H-benzimidazol-2-yl)sulfinyl]methyl]-2-pyridinamine,
 6-[[[5-(trifluoromethyl)-1H-benzimidazol-2-yl]sulfinyl]methyl]-2-pyridinamine,
 6-[[(5-methoxy-1H-benzimidazol-2-yl)sulfinyl]methyl]-2-pyridinamine,
 6-[[(5-ethoxy-1H-benzimidazol-2-yl)sulfinyl]methyl]-2-pyridinamine,
 6-[[(5,6-dimethyl-1H-benzimidazol-2-yl)sulfinyl]methyl]-2-pyridinamine,
 6-[[(4,6-dimethyl-1H-benzimidazol-2-yl)sulfinyl]methyl]-2-pyridinamine,
 6-[[(5,6-dimethoxy-1H-benzimidazol-2-yl)sulfinyl]methyl]-2-pyridinamine, and
 6-[[[5-(hydroxymethyl)-1H-benzimidazol-2-yl]sulfinyl]methyl]-2-pyridinamine; or a pharmaceutically acceptable addition salt thereof.

3. A pharmaceutical composition for treating ulcers in mammals comprising a therapeutically effective amount of a compound according to claim 1 together with a pharmaceutically acceptable carrier.

4. A pharmaceutical composition according to claim 3 wherein said compound is selected from the group consisting of:
 6-[(1H-benzimidazol-2-ylsulfinyl)methyl]-2-pyridinamine,
 6-[[(4-methyl-1H-benzimidazol-2-yl)sulfinyl]methyl]-2-pyridinamine,
 6-[[(5-methyl-1H-benzimidazol-2-yl)sulfinyl]methyl]-2-pyridinamine,
 6-[[(5-chloro-1H-benzimidazol-2-yl)sulfinyl]methyl]-2-pyridinamine,
 6-[[[5-(trifluoromethyl)-1H-benzimidazol-2-yl]sulfinyl]methyl]-2-pyridinamine,
 6-[[(5-methoxy-1H-benzimidazol-2-yl)sulfinyl]methyl]-2-pyridinamine,
 6-[[(5-ethoxy-1H-benzimidazol-2-yl)sulfinyl]methyl]-2-pyridinamine,
 6-[[(5,6-dimethyl-1H-benzimidazol-2-yl)sulfinyl]methyl]-2-pyridinamine,
 6-[[(4,6-dimethyl-1H-benzimidazol-2-yl)sulfinyl]methyl]-2-pyridinamine,
 6-[[(5,6-dimethoxy-1H-benzimidazol-2yl)sulfinyl]methyl]-2-pyridinamine, and
 6-[[[5-hydroxymethyl)-1H-benzimidazol-2-yl]sulfinylmethyl]-2-pyridinamine; or a pharmaceutically acceptable addition salt thereof.

5. A method for treating ulcers in mammals comprising administering a therapeutically effective amount of a compound according to claim 1 to a mammal in need of such treatment.

6. A method according to claim 5 wherein said compound is selected from the group consisting of:
 6-[(1H-benzimidazol-2-ylsulfinyl)methyl]-2-pyridinamine,
 6-[[(4-methyl-1H-benzimidazol-2-yl)sulfinyl]methyl]-2-pyridinamine,
 6-[[(5-methyl-1H-benzimidazol-2-yl)sulfinyl]methyl]-2-pyridinamine,
 6-[[(5-chloro-1H-benzimidazol-2-yl)sulfinyl]methyl]-2-pyridinamine,
 6-[[[5-(trifluoromethyl)-1H-benzimidazol-2-yl]sulfinyl]methyl]-2-pyridinamine,
 6-[[(5-methoxy-1H-benzimidazol-2-yl)sulfinyl]methyl]-2-pyridinamine,
 6-[[(5-ethoxy-1H-benzimidazol-2-yl)sulfinyl]methyl]-2-pyridinamine,
 6-[[(5,6-dimethyl-1H-benzimidazol-2-yl)sulfinyl]methyl]-2-pyridinamine,
 6-[[(4,6-dimethyl-1H-benzimidazol-2-yl)sulfinyl]methyl]-2-pyridinamine,
 6-[[(5,6-dimethoxy-1H-benzimidazol-2-yl)sulfinyl]methyl]-2-pyridinamine, and
 6-[[[5-(hydroxymethyl)-1H-benzimidazol-2-yl)sulfinylmethyl]-2-pyridinamine;
 or a pharmaceutically acceptable addition salt thereof.

* * * * *

UNITED STATES PATENT AND TRADEMARK OFFICE
CERTIFICATE OF CORRECTION

PATENT NO. : 4,772,619
DATED : Sept. 20, 1988
INVENTOR(S) : Adelstein et al.

Page 1 of 2

It is certified that error appears in the above-identified patent and that said Letters Patent is hereby corrected as shown below:

Columns 3 and 4, reaction scheme A, the last structure in column 3 and the first structure in column 4, reading

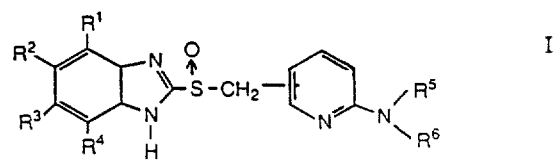   I

+

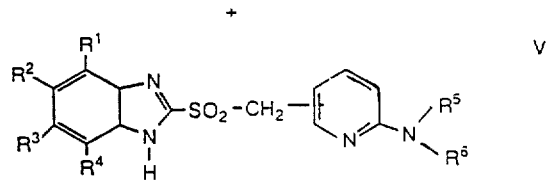   V should read

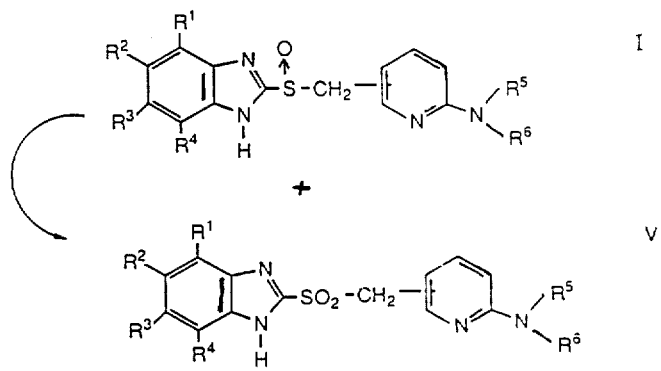

UNITED STATES PATENT AND TRADEMARK OFFICE
CERTIFICATE OF CORRECTION

PATENT NO. : 4,772,619

DATED : Sept. 20, 1988

INVENTOR(S) : Adelstein et al.

It is certified that error appears in the above-identified patent and that said Letters Patent is hereby corrected as shown below:

Column 9, line 61, reading "$(H^+ + ^+)$" should read -- $(H^+ + K^+)$ --.

Column 17, line 44, reading "$C_{14}H_{14}N_4SO$" should read -- $C_{14}H_{14}N_4SO_2$ --.

Signed and Sealed this

Twenty-third Day of October, 1990

Attest:

HARRY F. MANBECK, JR.

Attesting Officer

Commissioner of Patents and Trademarks